United States Patent

Trace

[11] Patent Number: 5,278,338
[45] Date of Patent: Jan. 11, 1994

[54] RACEMIZATION PROCESS FOR OPTICALLY ACTIVE CARBOXYLIC ACIDS, SALTS AND ESTERS

[75] Inventor: Rhonda L. Trace, Baton Rouge, La.

[73] Assignee: Ethyl Corporation, Richmond, Va.

[21] Appl. No.: 971,115

[22] Filed: Nov. 4, 1992

[51] Int. Cl.$^5$ .................. C07B 55/00; C07D 207/04; C07D 333/16

[52] U.S. Cl. .................. 562/401; 548/571; 548/572; 549/78; 549/79; 549/498; 549/499; 558/354; 560/10; 560/15; 560/17; 560/51; 560/56; 560/60; 560/61; 560/100; 560/102; 560/105; 560/121; 560/123; 560/124; 560/125; 560/128; 560/152; 560/226; 560/227; 560/265; 564/123; 564/162; 564/169; 564/180; 564/183; 564/189; 564/190; 564/209; 568/420; 568/426; 568/440; 568/442; 568/446; 568/449; 568/495

[58] Field of Search .............. 562/401; 548/571, 572; 549/78, 79, 498, 499; 558/354; 560/10, 15, 17, 51, 56, 60, 61, 100, 102, 105, 121, 123, 124, 125, 128, 152, 226, 227, 265; 564/123, 162, 169, 180, 183, 189, 190, 209; 568/420, 426, 440, 442, 446, 449, 495

[56] References Cited

U.S. PATENT DOCUMENTS 4,767,880 8/1988 Wullbrandt et al. .................. 562/61
4,769,486 9/1988 Harada et al. ....................... 562/401
5,145,992 9/1992 Mueller et al. ...................... 562/431

Primary Examiner—José G. Dees
Assistant Examiner—Vera C. Clarke
Attorney, Agent, or Firm—Richard J. Hammond

[57] ABSTRACT

A method for racemizing an optically active carboxylic acid, or ester thereof, of the formula:

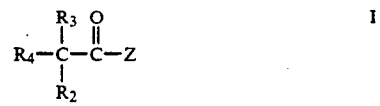

where $R_1$ is hydrogen, hydroxy, halo, cyano, $C_1$ to $C_6$ linear or branched alkoxy, amino or substituted amino or the group

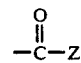

is nitrile; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, $C_6$ to $C_{10}$ aryl, $C_1$ to $C_6$ linear or branched alkoxy, $C_6$ to $C_{10}$ aryloxy, $C_1$ to $C_6$ alkylthio, $C_3$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, $C_{10}$ to $C_{14}$ aryl, or biphenyl unsubstituted or substituted with methyl or halo, comprising heating said optically active carboxylic acid or ester thereof in the presence of water at a temperature of from about 40° C. to about 200° C. in the presence of a catalytically effective amount of a compound of the formula $M(XO)_n$ where M is an alkali or alkaline earth metal, X is halogen, where n is 1 or 2 for a time sufficient to racemize said carboxylic acid or ester thereof.

6 Claims, No Drawings

RACEMIZATION PROCESS FOR OPTICALLY ACTIVE CARBOXYLIC ACIDS, SALTS AND ESTERS

FIELD OF THE INVENTION

This invention relates to a process for converting an enantiomeric form of certain aliphatic carboxylic acids into a racemic mixture of enantiomers. This invention specifically relates to the racemization of one of the enantiomers of profentype carboxylic acids or ester.

BACKGROUND OF THE INVENTION

Profen-types of compounds are typically defined as propionic acids (or esters) bearing at least one aromatic substituent, usually $\alpha$- to the carboxylic function.

These carboxylic acids have an asymmetric carbon atom (the carbon atom adjacent to the carbonyl group) that typically produces a racemic mixture of these acids [a mixture of both of the (+) and (−) or dextro and levo rotatory forms]. For example, ibuprofen [(2-(4-isobutylphenyl)propionic acid)], a commercially and pharmaceutically important chemical compound, is typically produced and sold as the racemic mixture. Many other of the pharmaceutically-active profen drugs are also produced as racemates and administered in this form. However, it is well known that the physiological utility of the racemic mixtures is almost exclusively focused on one enantiomer, the other having either no effect or even diminishing the effect of the active enantiomer. Thus the S(+) form of ibuprofen is physiologically active in reducing inflammation and in providing an analgesic effect. See, for example, U.S. Pat. Nos. 4,851,444 and 4,877,620. The R(−) enantiomer is devoid of activity for these indications, although it is, in part, converted in vivo into the S(+) compound. Other profens, i.e., naproxen, are only prescribed as the single enantiomer.

OBJECTS OF THE INVENTION

Disposal of the undesired enantiomer is not environmentally or economically desirable. Accordingly, it is an object of this invention to provide a process whereby the inactive or undesirable enantiomer of certain optically-active carbonyl compounds acids may be converted into the other usable, desirable enantiomer.

It is a further object of this invention to carry out the conversion of one enantiomer of these carbonyl compounds into the other enantiomer in an efficient and economical manner.

These and other objects of the present invention are more completely described hereafter in the description of the preferred embodiment.

DESCRIPTION OF THE PREFERRED EMBODIMENTS

The process of the present invention involves using one of the enantiomeric forms (or an enantiomerically enriched mixture) of a carbonyl-containing compound where the optically active center is $\alpha$- to the carbonyl formation as a starting material and subjecting this starting material to the process of the present invention whereby conversion of one enantiomer to the other is effected. It should be noted, however, that the present conversion process only functions to achieve a racemic mixture of the enantiomers, i.e. it is a racemization process.

The process involves racemizing the enantiomer in the presence of water at a temperature of from about 40° C. to about 200° C. Preferably, the process is carried out at about 45° C. to about 80° C., most preferably about 50° C. to about 60° C. The time of conversion to the racemic mixture is dramatically affected by adding to the aqueous solution a catalytically effective amount of an alkali or alkaline earth metal compound of the formula $M(XO)_n$ where M is an alkali or alkaline earth metal, X is a halogen (fluoro, chloro, bromo or iodo) and n is an integer that is 1 or 2. It is preferred that the compounds are those with potassium or sodium as the moiety M. of the preferred compounds; it is most preferred that X is chloro. Especially preferred in the process of the present equation is the compound sodium hypochlorite.

The carbonyl-containing compounds useful in the process of the present invention have the formula:

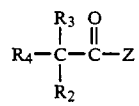

where Z is hydrogen, hydroxy, halo (e.g. chloro, bromo, fluoro), cyano, amino, sustituted amino (e.g. dialkyl; diaryl); or $C_1$ to $C_6$ linear or branched alkoxy or the group

is nitrile; $R_2$, $R_3$ and $R_4$ are different and are hydrogen or $C_1$ to $C_6$ linear or branched alkyl, e.g., methyl or ethyl; $C_1$ to $C_6$ linear or branched haloalkyl, e.g., chloromethyl, fluoromethyl, chloroethyl, fluoroethyl; aralkyl, e.g., benzyl; cycloalkyl, e.g., cyclopropyl, cyclobutyl, cyclopentyl, or cyclohexyl; alkyl substituted cycloalkyl, e.g., methylcyclohexyl; $C_6$ to $C_{10}$ aryl, e.g., phenyl unsubstituted or substituted with, for example, methyl, dimethyl, or butyl, especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., methoxy, ethoxy, propoxy, or butoxy; $C_6$ to $C_{10}$ aryloxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_3$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, or thienyl; or $C_{10}$ to $C_{14}$ aryl, e.g., naphthyl or naphthyl substituted with $C_1$ to $C_4$ alkyl, e.g., methyl, $C_1$ to $C_4$ alkoxy, e.g., ethoxy or halo; or biphenyl unsubstituted or substituted with methyl or halo, especially fluoro.

Preferred compounds of formula I are those of the formula:

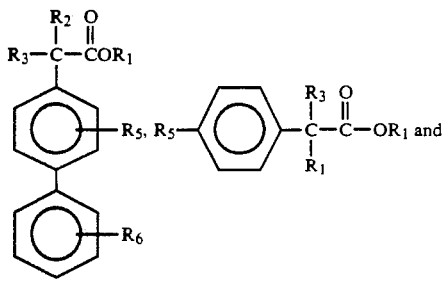

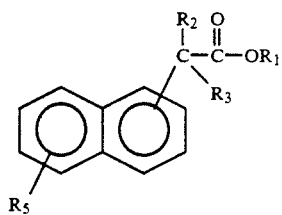

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The amount of the compound $M(XO)_n$ in solution can vary from about 0.01% to about 10.0% of such compound based on the mole % of carbonyl-containing acid enantiomer to be converted. Preferably, the amount of compound is from about 0.05 mole % to about 0.5 mole % based on moles of carbonyl compound, most preferably 0.075 mole % to about 0.25 mole %.

By using the above disclosed catalytic compound having the formula $M(XO)_n$, the time period to achieve a racemic mixture is reduced to from about 4 to about 24 hours, depending on the amount of excess enantiomer in the starting material. For example, with a starting material of 100% enantiomer, periods of conversion to the racemic mixture are about 20 to 24 hours. Enantiomerically enriched starting materials reach the racemization maximum more quickly, e.g., a composition comprising 70% R(−) enantiomer and 30% S (+) enantiomer will achieve the 50:50 racemization in about 10 to about 12 hours.

As indicated above, the process of the present invention is useful for conversion of one of the enantiomeric forms of the disclosed carbonyl-containing compound into the other only up to the point of achieving a racemic mixture of enantiomers. The racemic mixture is, of course, useful as is or it may be subject to other processes to separate the enantiomeric mixture.

EXAMPLES

The following examples are illustrative of the process of the present invention.

General Procedure

The racemization of the sodium salt of S(+) 2-(4-isobutylphenyl) propionic acid was carried out by dissolving 0.5 g of the salt in a saturated aqueous solution of 40 ml of NaOCl. The solution was heated to the desired temperature and, after 1 hour, acidified with dilute hydrochloric acid (about 5%) and extracted with ether. After evaporation of the solvent, the residues were analyzed by HPLC. The following results were obtained:

| Example Number | Temperature | % Racemization |
| --- | --- | --- |
| 1 | 45 | 10%* |
| 2 | 60 | 5% |
| 3 | 80 | 10% |

*Experiment was carried out for about 5 minutes only

I claim:

1. A method for racemizing an optically active carboxylic acid, ester or salt thereof, of the formula:

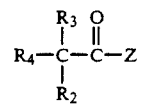

where Z is hydrogen, hydroxy, halo, cyano, $C_1$ to $C_6$ linear or branched alkoxy, amino or substituted amino or the group

is nitrile; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, phenyl unsubstituted or substituted with methyl, dimethyl, butyl, isobutyl, $C_1$ to $C_4$ alkylthio, $C_1$ to $C_4$ alkoxy, cyano or halo, $C_1$ to $C_6$ linear or branched alkoxy, $C_6$ to $C_{10}$ aryloxy, $C_1$ to $C_6$ alkylthio, $C_3$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, naphthyl or naphthyl substituted with $C_1$ to $C_4$ alkyl, $C_1$ to $C_4$ alkoxy, or halo, or biphenyl unsubstituted or substituted with methyl or halo, comprising heating an aqueous solution of said optically active carboxylic acid, ester or salt thereof at a temperature of from about 40° C. to about 200° C. in the presence of a catalytically effective amount of a compound of the formula $M(XO)_n$ where M is an alkali or alkaline earth metal, X is halogen, where n is 1 or 2 for a time sufficient to racemize said carboxylic acid, salt or ester thereof.

2. The method according to claim 1 wherein said temperature is from about 45° C. to about 80° C.

3. The method according to claim 2 wherein said temperature is from about 50° C. to about 60° C.

4. A method for racemizing R(−)-ibuprofen comprising heating an aqueous solution of said ibuprofen at a temperature of from about 40° C. to about 200° C. in the presence of a catalytically effective amount of a compound of the formula $M(XO)_n$ where M is an alkali or alkaline earth metal, X is halogen, where n is 1 or 2 for a time sufficient to racemize said ibuprofen.

5. The method according to claim 4 wherein said temperature is from about 45° C. to about 80° C.

6. The method according to claim 4 wherein said temperature is from about 50° C. to about 60° C.

* * * * *